(12) United States Patent
Rong

(10) Patent No.: US 12,040,074 B2
(45) Date of Patent: Jul. 16, 2024

(54) SYSTEMS AND METHODS FOR DATA SYNCHRONIZATION

(71) Applicant: SHANGHAI UNITED IMAGING HEALTHCARE CO., LTD., Shanghai (CN)

(72) Inventor: Chengcheng Rong, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 409 days.

(21) Appl. No.: 17/172,095

(22) Filed: Feb. 10, 2021

(65) Prior Publication Data

US 2021/0257108 A1  Aug. 19, 2021

(30) Foreign Application Priority Data

Feb. 18, 2020  (CN) .......................... 202010099414.X

(51) Int. Cl.
| | | |
|---|---|---|
| *A61N 5/00* | (2006.01) | |
| *G06K 7/14* | (2006.01) | |
| *G06T 7/00* | (2017.01) | |
| *G06V 10/25* | (2022.01) | |
| *G16H 30/20* | (2018.01) | |
| *G16H 30/40* | (2018.01) | |
| *G16H 80/00* | (2018.01) | |

(52) U.S. Cl.
CPC .......... *G16H 30/20* (2018.01); *G06K 7/1417* (2013.01); *G06T 7/0012* (2013.01); *G06V 10/25* (2022.01); *G16H 30/40* (2018.01); *G16H 80/00* (2018.01)

(58) Field of Classification Search
CPC ......... G16H 30/20; G16H 30/40; G06V 10/25
See application file for complete search history.

(56) References Cited

U.S. PATENT DOCUMENTS

| | | |
|---|---|---|
| 2004/0103169 A1 | 5/2004 | Nolte |
| 2012/0136194 A1 | 5/2012 | Zhang et al. |
| 2012/0166391 A1 | 6/2012 | Liu et al. |

(Continued)

FOREIGN PATENT DOCUMENTS

| | | |
|---|---|---|
| CN | 101141620 A | 3/2008 |
| CN | 101697502 A | 4/2010 |

(Continued)

OTHER PUBLICATIONS

The Second Office Action in Chinese Application No. 202010099414.X dated Dec. 1, 2021, 12 pages.

(Continued)

*Primary Examiner* — Reginald R Reyes
(74) *Attorney, Agent, or Firm* — METIS IP LLC

(57) ABSTRACT

A system for data synchronization is provided. The system may include a workstation, a user terminal, and a storage device that is accessible to the user terminal and the workstation. The workstation may be configured to generate an identifier relating to a subject. The identifier may point to a data address in the storage device that stores data relating to the subject. The user terminal may be configured to acquire image data of the subject from the data address based on the identifier, receive a user input with respect to the image data of the subject, and update the image data stored in the data address based on the user input.

16 Claims, 8 Drawing Sheets

(56) References Cited

U.S. PATENT DOCUMENTS

| | | | |
|---|---|---|---|
| 2017/0329847 A1 | 11/2017 | Qui | |
| 2017/0332130 A1* | 11/2017 | Park | H04N 21/485 |
| 2020/0185079 A1 | 6/2020 | Yan et al. | |
| 2020/0228747 A1* | 7/2020 | Ventura | H04N 21/4223 |
| 2020/0273552 A1* | 8/2020 | Wolf | A61B 17/00 |
| 2021/0209757 A1* | 7/2021 | Min | G06T 7/0012 |

FOREIGN PATENT DOCUMENTS

| | | |
|---|---|---|
| CN | 201780586 U | 3/2011 |
| CN | 202995733 U | 6/2013 |
| CN | 103488904 A | 1/2014 |
| CN | 103593110 | 2/2014 |
| CN | 103745126 A | 4/2014 |
| CN | 103761623 A | 4/2014 |
| CN | 104092757 A | 10/2014 |
| CN | 104092811 A | 10/2014 |
| CN | 104281683 A | 1/2015 |
| CN | 104320491 A | 1/2015 |
| CN | 104820932 A | 8/2015 |
| CN | 104980519 | 10/2015 |
| CN | 106202410 A | 12/2016 |
| CN | 106997421 A | 8/2017 |
| CN | 107392897 A | 11/2017 |
| CN | 108053869 | 5/2018 |
| CN | 108231145 A | 6/2018 |
| CN | 109636424 A | 4/2019 |
| CN | 109769079 A | 5/2019 |
| CN | 109803111 A | 5/2019 |
| CN | 109949352 A | 6/2019 |
| CN | 109961830 A | 7/2019 |
| CN | 110164529 A | 8/2019 |
| CN | 110232663 A | 9/2019 |
| CN | 110517254 A | 11/2019 |
| IN | 201617041325 A | 3/2017 |
| KR | 20150097250 A | 8/2015 |
| KR | 20160010660 A | 1/2016 |
| WO | 2016178508 A1 | 11/2016 |
| WO | 2017050011 A1 | 3/2017 |

OTHER PUBLICATIONS

The Third Office Action in Chinese Application No. 202010099414.X dated Apr. 2, 2022, 18 pages.

* cited by examiner

SYSTEMS AND METHODS FOR DATA SYNCHRONIZATION

CROSS-REFERENCE TO RELATED APPLICATIONS

This application claims priority of Chinese Patent Application No. 202010099414.X, filed on Feb. 18, 2020, the contents of which are hereby incorporated by reference.

TECHNICAL FIELD

The present disclosure generally relates to data processing, and more particularly, relates to systems and methods for data synchronization between a user terminal and a workstation.

BACKGROUND

A medical system (e.g., a medical imaging system, a medical treatment system) usually includes a workstation for data processing and a user terminal for enabling user interaction. For example, a user may input data regarding a subject (e.g., a patient) into the user terminal, and the workstation may process the data inputted by the user and/or other data relating to the subject. In some occasions, data synchronization needs to be performed between the user terminal and the workstation.

SUMMARY

According to one aspect of the present disclosure, a system for data synchronization is provided. The system may include a workstation, a user terminal, and a storage device that is accessible to the user terminal and the workstation. The workstation may be configured to generate an identifier relating to a subject. The identifier may point to a data address in the storage device that stores data relating to the subject. The user terminal may be configured to acquire image data of the subject from the data address based on the identifier, receive a user input with respect to the image data of the subject, and update the image data stored in the data address based on the user input.

In some embodiments, the user input may include an annotation regarding a region of interest (ROI) of the subject in the image data.

In some embodiments, the workstation may be further configured to acquire the updated image data stored in the data address and generate a processing result by processing the updated image data. The processing result may include a treatment plan directed to the ROI.

In some embodiments, the data stored in the data address may include a plurality of candidate images of the subject. To acquire the image data of the subject based on the identifier, the user terminal may be configured to access the data address based on the identifier, and select a target image from the plurality of candidate images stored in the data address.

In some embodiments, to acquire image data of the subject from the data address based on the identifier, the user terminal may be configured to obtain the image data of the subject by scanning the identifier.

In some embodiments, the user terminal may be configured to generate the updated image data based on the image data of the subject and the user input, access the data address based on the identifier, and store the updated image data into the data address.

In some embodiments, the identifier may include at least one of a barcode, a quick response (QR) code, a text identifier, or an image identifier.

In some embodiments, the user terminal may be further configured to determine an input setting with respect to the user input based on feature information relating to the subject.

In some embodiments, the user input may be inputted into the user terminal via a handwriting pen.

In some embodiments, the storage device may be part of the workstation.

According to another aspect of the present disclosure, a method for data synchronization implemented on a user terminal is provided. The user terminal may be communicated with a storage device that is accessible to the user terminal and a workstation. The method may include acquiring image data of the subject from a data address in the storage device that stores data relating to the subject based on an identifier relating to a subject. The identifier may be generated by the workstation and points to the data address. The method may also include receiving a user input with respect to the image data of the subject, and updating the image data stored in the data address based on the user input.

According to another aspect of the present disclosure, a method for data synchronization implemented on a workstation is provided. The workstation may be communicated with a storage device that is accessible to the workstation and a user terminal. The method may include generating an identifier relating to the subject. The identifier may point to a data address in the storage device that stores data relating to the subject. Image data of the subject may be acquired by the user terminal from the data address based on the identifier. A user input with respect to the image data of the subject may be received by the user terminal. The image data stored in the data address may be updated by the user terminal based on the user input. The method may also include acquiring the updated image data stored in the data address and generate a processing result by processing the updated image data.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, sections or assembly of different levels in ascending order. However, the terms may be displaced by another expression if they achieve the same purpose.

Figure 2:
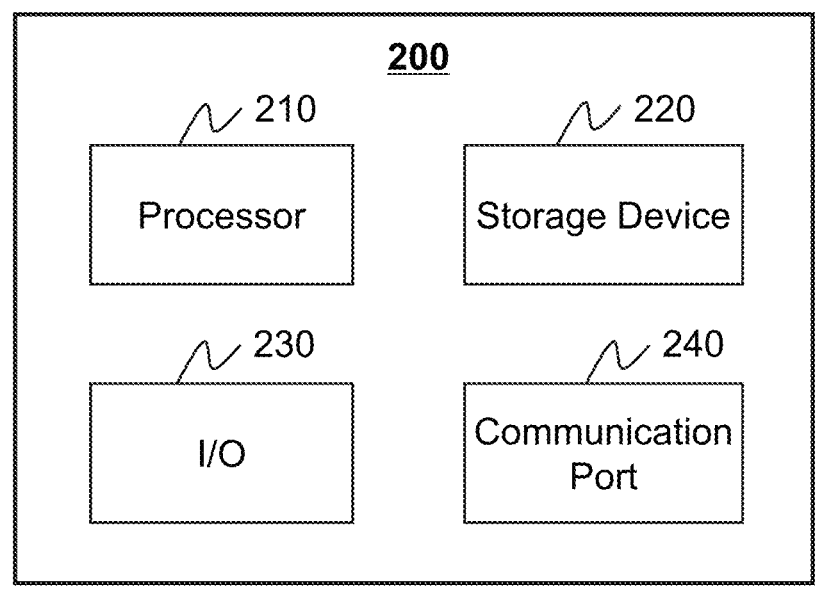
FIG. 2 is a schematic diagram illustrating exemplary hardware and/or software components of a computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 210 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module, or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items. The term "image" in the present disclosure is used to collectively refer to image data (e.g., scan data, projection data) and/or images of various forms, including a two-dimensional (2D) image, a three-dimensional (3D) image, a four-dimensional (4D) image, etc.

It will be understood that, although the terms "first," "second," "third," etc., may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

Provided herein are systems and methods for data synchronization. For illustration purposes, the following descriptions are described with reference to data synchronization in a medical system (e.g., a medical imaging system, a medical treatment system). For example, the medical imaging system may be a non-invasive biomedical imaging system. In some embodiments, the medical imaging system may include a single modality imaging system and/or a multi-modality imaging system. The single modality imaging system may include, for example, an ultrasound imaging system, an X-ray imaging system, an computed tomography (CT) system, a magnetic resonance imaging (MRI) system, an ultrasonography system, a positron emission tomography (PET) system, an optical coherence tomography (OCT) imaging system, an ultrasound (US) imaging system, an intravascular ultrasound (IVUS) imaging system, a near infrared spectroscopy (NIRS) imaging system, a far infrared (FIR) imaging system, or the like, or any combination thereof. The multi-modality imaging system may include, for example, an X-ray imaging-magnetic resonance imaging (X-ray-MRI) system, a positron emission tomography-X-ray imaging (PET-X-ray) system, a single photon emission computed tomography-magnetic resonance imaging (SPECT-MRI) system, a positron emission tomography-computed tomography (PET-CT) system, a C-arm system, a digital subtraction angiography-magnetic resonance imaging (DSA-MRI) system, etc. The medical treatment system may include a radiotherapy (RT) system. It should be noted that the medical system described below is merely provided for illustration purposes, and not intended to limit the scope of the present disclosure. The systems and methods for data synchronization disclosed herein may be applied to any system other than a medical system.

The term "imaging modality" or "modality" as used herein broadly refers to an imaging method or technology that gathers, generates, processes, and/or analyzes imaging information of a subject. The subject may include a biological subject and/or a non-biological subject. The biological subject may be a human being, an animal, a plant, or a portion thereof (e.g., a cell, a tissue, an organ, etc.). In some embodiments, the subject may be a man-made composition of organic and/or inorganic matters that are with or without life.

A medical imaging system usually includes a workstation for data processing and a user terminal for enabling user interaction. In some occasions, data synchronization needs to be performed between the user terminal and the workstation. For example, an RT system, which includes a user terminal and a workstation, is widely used in clinical treatment for cancers and other conditions. Conventionally, before a radiotherapy treatment is performed on a cancer patient, a planning image (e.g., a CT image, an MMRI image) of the cancer patient may be acquired using an imaging device. A treatment plan for the cancer patient may be made based on the planning image. Normally, the user terminal (e.g., a tablet, a mobile phone, a drawing board) may be configured to display the planning image, and a user (e.g., a doctor) may need to annotate a contour of a target (e.g., a tumor) and/or an organ-at-risk (OAR) in the planning image. Due to the limited hardware capabilities of the user terminal, the annotated image may be transmitted to the workstation for further processing, for example, generating the treatment plan. In this process, data need to be synchronized between the user terminal and the workstation. For example, if a storage device is connected to a local area network (LAN), the user terminal and the workstation have to connect to the LAN and get an access permission to the storage device, so as to acquire data from the storage device. If the user terminal modifies the acquired data, it may need to upload the modified data to the storage device, and the workstation may need to connect to the LAN and get the access permission to the storage device to acquire the modified data, which has a low efficiency. Thus, it may be desirable to develop effective systems and methods for synchronizing data between the user terminal and the workstation.

An aspect of the present disclosure relates to a system and method for data synchronization. The system may include a workstation, a user terminal, and a storage device that is accessible to the user terminal and the workstation. The workstation may be configured to generate an identifier relating to the subject. The identifier may point to a data address in the storage device that stores data relating to the subject, The user terminal may be configured to acquire image data of the subject from the data address based on the identifier, receive a user input with respect to the image data of the subject, and update the image data stored in the data address based on the user input. The workstation may be further configured to acquire the updated image data stored in the data address and generate a processing result by processing the updated image data.

According to some embodiments of the present disclosure, the user terminal may access the data address corresponding to the subject by scanning the identifier pointing to the data address to obtain the image data from the data address. After the updated image data is generated by the user terminal, the user terminal may automatically transmit the updated image data to the storage device to be stored in the data address. After the updated image data is stored in the data address, it may be transmitted to the workstation automatically. In some embodiments, the storage device may be part of the workstation. For example, the storage device may be a cache region of the workstation shared with the user terminal. The user terminal may have a permission to access data stored in the cache region and/or upload data into the cache region. In such cases, once the user terminal generates new data based on a user input (e.g., an updated image of a subject with an annotation regarding a region of interest (ROI) of the subject), it can upload the new data into the cache region, and the new data may be automatically synchronized with the workstation. Thus, through the storage device, data synchronization between the workstation and the user terminal may be realized, which may effectively prevent loss of data (e.g., because the new data generated by the user terminal may be transmitted to the storage device automatically) and improve the efficiency of the data transmission and the data synchronization.

Figure 1:
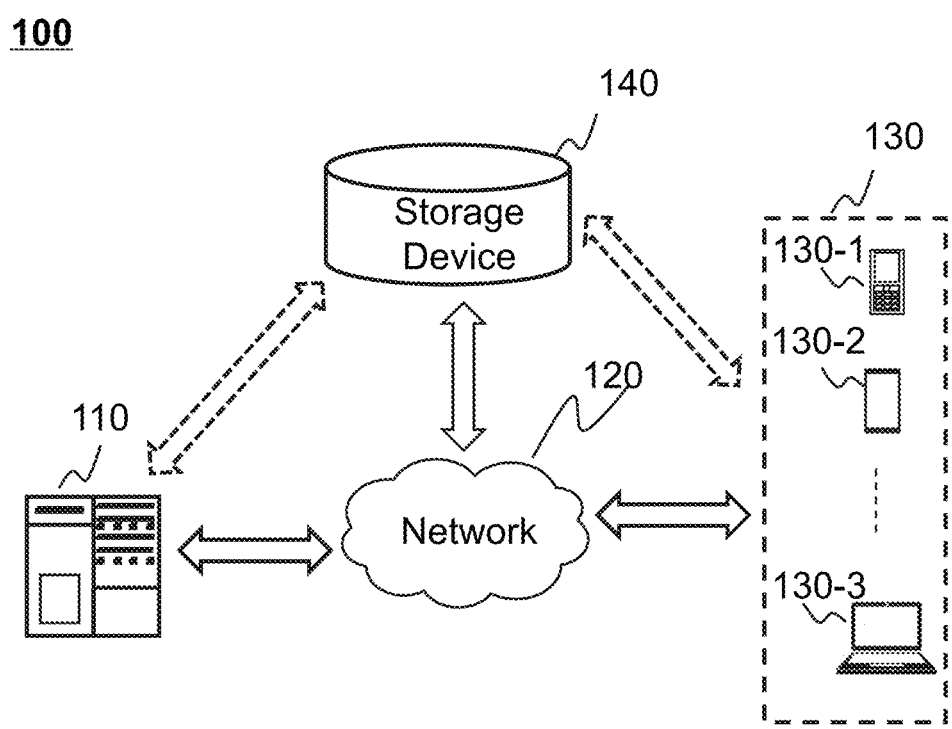
FIG. 1 is a schematic diagram illustrating an exemplary data synchronization system according to some embodiments of the present disclosure.

FIG. 1 is a schematic diagram illustrating an exemplary data synchronization system 100 according to some embodiments of the present disclosure. The system 100 may include a workstation 110, a network 120, a user terminal 130, and a storage device 140. The data synchronization system 100 may be used to achieve data synchronization between the workstation 110 and the user terminal 130 via the storage device 140, which is connected to both the workstation 110 and the user terminal 130. For example, as shown in FIG. 1, the workstation 110 may be connected to the storage device 140 directly or via the network 120; and the user terminal 130 may be connected to the storage device 140 directly or via the network 120. Optionally, the workstation 110 and the user terminal 130 may be connected to each other directly or via the network 120.

The workstation 110 may be configured to process information obtained from the user terminal 120 and/or the storage device 140. For example, the workstation 110 may generate an identifier relating to a subject (e.g., a patient). The identifier may point to a data address in the storage device 140 that stores data relating to the subject. As another example, the workstation 110 may acquire updated image data stored in the data address. As another example, the workstation 110 may generate a processing result by processing the updated image data.

In some embodiments, the workstation 110 may be a single server or a server group. The server group may be centralized or distributed. In some embodiments, the workstation 110 may be local or remote. For example, the workstation 110 may access information stored in the user terminal 120 and/or the storage device 140 via the network 120. As another example, the workstation 110 may be directly connected to the user terminal 120 and/or the storage device 140 to access stored information. In some embodiments, the workstation 110 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the workstation 110 may be implemented by a computing device 200 having one or more components as illustrated in FIG. 2.

In some embodiments, the workstation 110 may include one or more processors (e.g., single-core processor(s) or multi-core processor(s)). Merely by way of example, the workstation 110 may include a central processing unit (CPU), an application-specific integrated circuit (ASIC), an application-specific instruction-set processor (ASIP), a graphics processing unit (GPU), a physics processing unit (PPU), a digital signal processor (DSP), a field-programmable gate array (FPGA), a programmable logic device (PLD), a controller, a microcontroller unit, a reduced instruction-set computer (RISC), a microprocessor, or the like, or any combination thereof.

In some embodiments, the workstation 110 may have more powerful computing capability than the user terminal 130. For example, the workstation 110 may have a larger memory space, a better multitasking capability, a better capacity of manipulating different types of complex data, etc., or any combination thereof, than the user terminal 130 In some embodiments, the workstation 110 may be configured to execute a complex computational task. For example, the workstation 110 may be configured to generate a 3D image based on medical image data of a subject acquired by a biomedical imaging system as described elsewhere in this disclosure. As another example, the workstation 110 may be configured to generate a treatment plan for the subject based on the 3D image of the subject. As used herein, the complex computational task may include, for example, a computational task that needs a certain amount of computation resources (e.g., occupies a certain amount of storage space), a computational task that involves a certain amount of computation, or the like. Because the workstation 110 has a more powerful computing capability than the user terminal 130, it may take the workstation 110 less time to execute a complex computational than the user terminal 130.

Figure 3:
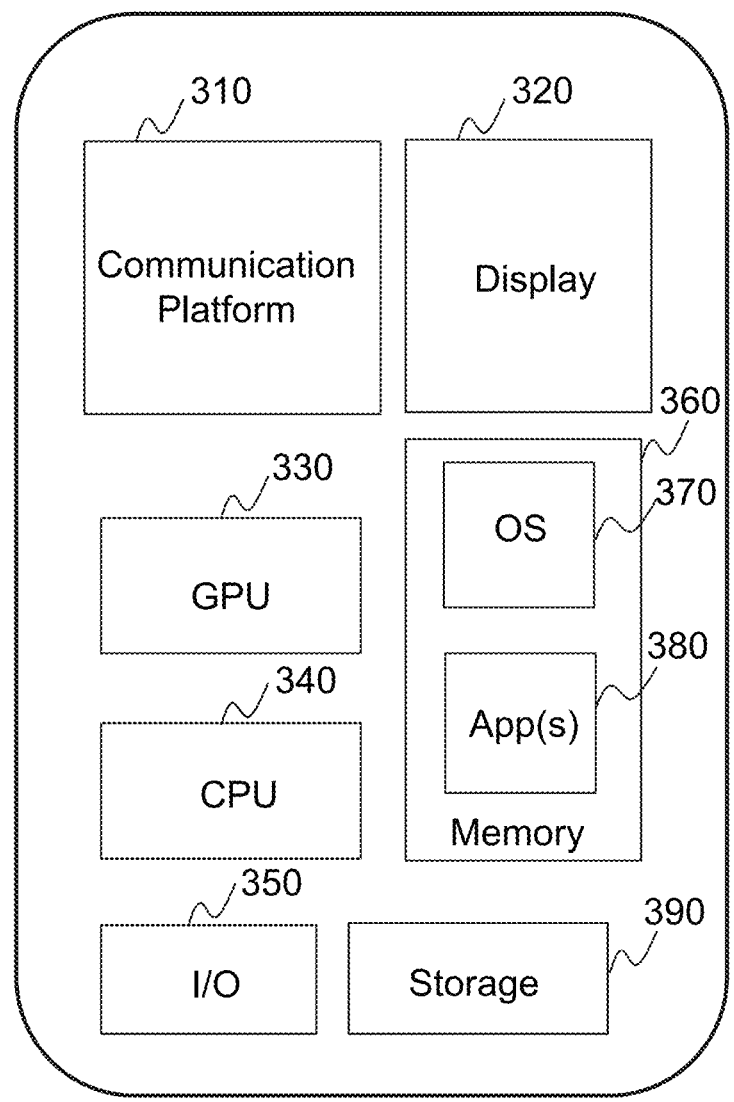
FIG. 3 is a schematic diagram illustrating exemplary hardware and/or software components of a mobile device according to some embodiments of the present disclosure.

The user terminal 130 may enable user interaction between a user and the data synchronization system 100. For example, the user terminal 130 may obtain image data of the subject from the storage device 140 and display the image data to the user. As another example, the user terminal 130 may receive a user input with respect to the image data of the subject, for example, a contour of an ROI of the subject inputted by the user. In some embodiments, the user terminal 130 may include a mobile device 130-1, a tablet computer 130-2, a laptop computer 130-3, or the like, or any combination thereof. In some embodiments, the mobile device 130-1 may include a smart home device, a wearable device, a mobile device, a virtual reality device, an augmented reality device, or the like, or any combination thereof. Merely by way of example, the user terminal 130 may include a mobile device as illustrated in FIG. 3. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, footwear, eyeglasses, a helmet, a watch, clothing, a backpack, a smart accessory, or the like, or any combination thereof. In some embodiments, the mobile device may include a mobile phone, a personal digital assistant (PDA), a gaming device, a navigation device, a point of sale (POS) device, a laptop, a tablet computer, a desktop, a drawing board, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™, an Oculus Rift™, a Hololens™, a Gear VR™, etc. In some embodiments, the user terminal 130 may include a camera.

In some embodiments, the user terminal 130 and the workstation 110 may be installed with one or more software, respectively. For example, the user terminal 130 may be installed with an interactive application, via which the user may interact with the user terminal 130 and/or other components of the data synchronization system 100. For example, the user terminal 130 may be installed with an annotation application, via which the user may annotate a contour of an ROI in the image data of the subject. The workstation 110 may be installed with one or more data processing applications. For example, the workstation 110 may be installed with a treatment plan application used for treatment planning and/or an image reconstruction application used for image reconstruction.

The network 120 may include any suitable network that can facilitate the exchange of information and/or data for the data synchronization system 100. In some embodiments, one or more components of the data synchronization system 100 (e.g., the workstation 110, the user terminal 130, the storage device 140, etc.) may communicate information and/or data with one or more other components of the data synchronization system 100 via the network 120. For example, both the user terminal 130 and the workstation 110 may be able to access data stored in the storage device 140 via the network 120.

The network 120 may be or include a public network (e.g., the Internet), a private network (e.g., a local area network (LAN)), a wired network, a wireless network (e.g., an 802.11 network, a Wi-Fi network), a frame relay network, a virtual private network (VPN), a satellite network, a telephone network, routers, hubs, switches, server computers, and/or any combination thereof. For example, the network 120 may include a cable network (e.g., an Ethernet, a universal serial bus (USB) data line), a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the data synchronization system 100 may be connected to the network 120 to exchange data and/or information.

In some embodiments, the workstation 110 and the storage device 140 may be connected to each other via a first network, and the user terminal 130 and the storage device 140 may be connected to each other via a second network. The first network and the second network may be the same or different. For example, the first network may be a wired network, such as an electrical cable, an optical cable; and the second network may be a wireless network, such as a Bluetooth™ link, a Wi-Fi™ link.

The storage device 140 may store data, instructions, and/or any other information. For example, the storage device 140 may store a medical examination plan, a treatment plan, data relating to the subject, or the like, or any combination thereof. The data relating to the subject may include basic data, medical record data, medical examination data, image data of the subject, or the like, or any combination thereof. The basic data may include, for example, a name, a gender, a nickname, an age, a phone number, an identity (ID) card number, a bed number, a room number, a head portrait, a fingerprint, a photo, or the like, or any combination thereof, of the subject. The medical record data may include, for example, a position of a lesion (e.g., a tumor), a disease type (e.g., a malignant tumor, a benign tumor), a treatment history, or the like, or any combination thereof. The medical examination data may include, for example, blood examination data, cell examination data. The image data of the subject may include, for example, one or more images (e.g., a CT image, an MRI image) of the subject (or a portion thereof).

In some embodiments, the storage device 140 may store data obtained from the workstation 110 and/or the user terminal 130. For example, the storage device 140 may store information inputted by a user via the user terminal 130. As another example, the storage device 140 may store a processing result (e.g., a treatment plan) generated by the workstation 110. In some embodiments, the storage device 140 may store data and/or instructions that the workstation 110 and/or the user terminal 130 may execute or use to perform exemplary methods described in the present disclosure. In some embodiments, the storage device 140 may include a mass storage device, a removable storage device, a volatile read-and-write memory, a read-only memory (ROM), or the like, or any combination thereof. Exemplary mass storage devices may include a magnetic disk, an optical disk, a solid-state drive, etc. Exemplary removable storage devices may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 140 may be connected to the network 120 to communicate with one or more other components of the data synchronization system 100 (e.g., the workstation 110, the user terminal 130). One or more components of the data synchronization system 100 may access the data and/or instructions stored in the storage device 140 via the network 120. In some embodiments, the storage device 140 may be directly connected to or communicate with one or more other components of the data synchronization system 100 (e.g., the workstation 110, the user terminal 130). In some embodiments, the storage device 140 may be part of the workstation 110.

In some embodiments, the storage device 140 may be part of the workstation 110. For example, the storage device 140 may be a cache region of the workstation shared with the user terminal. The user terminal 130 may access the storage device 140 and acquire image data of the subject from the storage device 140. The user terminal 130 may update the image data of the subject based on a user input and transmit the updated image data to the storage device 140. The updated image data may be stored in the storage device 140 and then be shared to the workstation 110. Conventionally, the user terminal 130 and the workstation 110 may need to connect to an LAN that connects the storage device 140 and get an access permission to the storage device 140, so as achieve a data synchronization between the user terminal 130 and the workstation 110. Compared to the conventional approach, the data synchronization system 100 may realize a more effective and safer data synchronization.

This description is intended to be illustrative, and not to limit the scope of the present disclosure. Many alternatives, modifications, and variations will be apparent to those skilled in the art. The features, structures, methods, and characteristics of the exemplary embodiments described herein may be combined in various ways to obtain additional and/or alternative exemplary embodiments. However, those variations and modifications do not depart the scope of the present disclosure. In some embodiments, the data synchronization system 100 may include one or more additional components and/or one or more components described above may be omitted. Additionally or alternatively, two or more components of the data synchronization system 100 may be integrated into a single component. For example, a component of the data synchronization system 100 may be replaced by another component that can implement the functions of the component.

FIG. 2 is a schematic diagram illustrating exemplary hardware and/or software components of a computing device 200 according to some embodiments of the present disclosure. The computing device 200 may be used to implement any component of the data synchronization system 100 as described herein. For example, the workstation 110 and/or the user terminal 130 may be implemented on the computing device 200, respectively, via its hardware, software program, firmware, or a combination thereof. Although only one such computing device is shown, for convenience, the computer functions relating to the data synchronization system 100 as described herein may be implemented in a distributed fashion on a number of similar platforms, to distribute the processing load. As illustrated in FIG. 2, the computing device 200 may include a processor 210, a storage device 220, an input/output (I/O) 230, and a communication port 240.

The processor 210 may execute computer instructions (e.g., program code) and perform functions of the workstation 110 and/or the user terminal 130 in accordance with techniques described herein. The computer instructions may include, for example, routines, programs, objects, components, data structures, procedures, modules, and functions, which perform particular functions described herein. For example, the processor 210 may process image data obtained from the user terminal 130, the storage device 140, and/or any other component of the data synchronization system 100. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors, thus operations and/or method operations that are performed by one processor as described in the present disclosure may also be jointly or separately performed by the multiple processors. For example, if in the present disclosure the processor of the computing device 200 executes both operation A and operation B, it should be understood that operation A and operation B may also be performed by two or more different processors jointly or separately in the computing device 200 (e.g., a first processor executes operation A and a second processor executes operation B, or the first and second processors jointly execute operations A and B).

The storage device 220 may store data/information obtained from the workstation 110, the user terminal 130, the storage device 140, and/or any other component of the data synchronization system 100. In some embodiments, the storage device 220 may include a mass storage device, a removable storage device, a volatile read-and-write memory, a read-only memory (ROM), or the like, or any combination thereof. In some embodiments, the storage device 220 may store one or more programs and/or instructions to perform exemplary methods described in the present disclosure.

The I/O 230 may input and/or output signals, data, information, etc. In some embodiments, the I/O 230 may enable a user interaction with the workstation 110 and/or the user terminal 130. In some embodiments, the I/O 230 may include an input device and an output device. The input device may include alphanumeric and other keys that may be input via a keyboard, a touch screen (for example, with haptics or tactile feedback), a speech input, an eye tracking input, a brain monitoring system, or any other comparable input mechanism. The input information received through the input device may be transmitted to another component (e.g., the workstation 110 and/or the user terminal 130) via, for example, a bus, for further processing. Other types of the input device may include a cursor control device, such as a mouse, a trackball, or cursor direction keys, etc. The output device may include a display (e.g., a liquid crystal display (LCD), a light-emitting diode (LED)-based display, a flat panel display, a curved screen, a television device, a cathode ray tube (CRT), a touch screen), a speaker, a printer, or the like, or a combination thereof.

The communication port 240 may be connected to a network (e.g., the network 120) to facilitate data communications. The communication port 240 may establish connections between the workstation 110, the user terminal 130, and/or the storage device 140. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee™ link, a mobile network link (e.g., 3G, 4G, 5G), or the like, or a combination thereof. In some embodiments, the communication port 240 may be and/or include a standardized communication port, such as RS232, RS485, etc. In some embodiments, the communication port 240 may be a specially designed communication port. For example, the communication port 240 may be designed in accordance with the digital imaging and communications in medicine (DICOM) protocol.

FIG. 3 is a schematic diagram illustrating exemplary hardware and/or software components of a mobile device 300 according to some embodiments of the present disclosure. In some embodiments, one or more components (e.g., a user terminal 130) of the data synchronization system 100 may be implemented on the mobile device 300.

As illustrated in FIG. 3, the mobile device 300 may include a communication platform 310, a display 320, a graphics processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS™, Android™, Windows Phone™) and one or more applications 380 may be loaded into the memory 360 from the storage 390 in order to be executed by the CPU 340. The applications 380 may include a browser or any other suitable mobile apps for receiving and rendering information relating to image processing or other information relating to the data synchronization system 100. User interactions with the information stream may be achieved via the I/O 350 and provided to the workstation 110, the user terminal 130, and/or other components of the data synchronization system 100 via the network 120.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal device. A computer may also act as a server if appropriately programmed.

Figure 4:
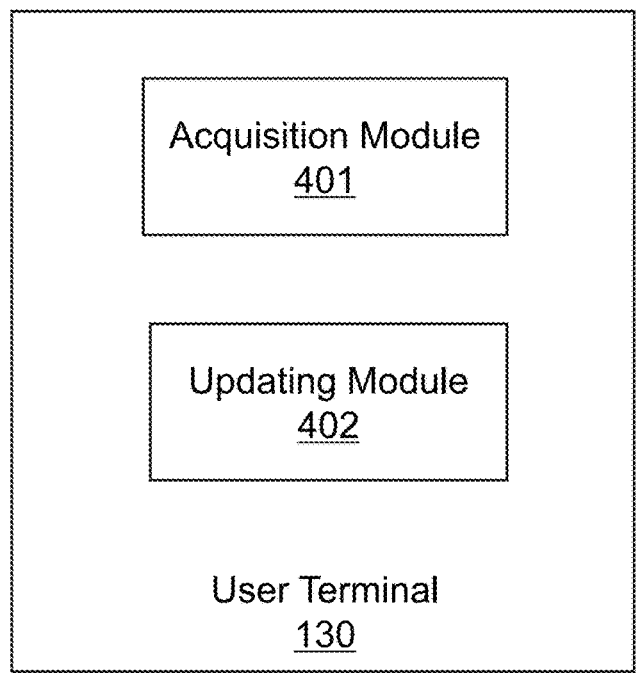
FIG. 4 is a block diagram illustrating an exemplary user terminal according to some embodiments of the present disclosure.

FIG. 4 is a block diagram illustrating an exemplary user terminal 130 according to some embodiments of the present disclosure. The user terminal 130 may be communicated with the storage device 140 that is accessible to the user terminal 130 and the workstation 110. As shown in FIG. 4, the user terminal 130 may include an acquisition module 401 and an updating module 402.

The acquisition module 401 may be configured to acquire image data of a subject from a data address in the storage device 140 that stores data of the subject based on an identifier. As used herein, the subject may include a biological subject (e.g., a patient) and/or a non-biological subject. In some embodiments, the subject may include an ROI. For example, the image data may include one or more images of the subject (or a portion thereof) acquired by a biomedical imaging system as described elsewhere in this disclosure. In some embodiments, the acquisition module 401 may access to the data address based on the identifier, and then obtain the image data from the data address.

The acquisition module 401 may also be configured to receive a user input with respect to the image data of the subject. The user input may include, for example, an annotation added to the target image, a modification of the target image, a confirmation regarding the target image, a comment regarding the target image, or the like, or any combination thereof. For example, the user input may include an annotation regarding the ROI of the subject in the image data. More descriptions regarding the acquisition of the image data and the user input may be found elsewhere in the present disclosure. See, e.g., 602, 603, and relevant descriptions thereof.

The updating module 402 may be configured to update the image data stored in the data address based on the user input. In some embodiments, the updating module 402 may generate the updated image data based on the image data of the subject and the user input. For example, the updating module 402 may add the annotation regarding the ROI to the target image, and the updated image data may include the target image with the annotation. In some embodiments, the updating module 402 may access the data address based on the identifier, and store the updated image data into the data address. In some embodiments, after the updated image data is generated, the updating module 402 may automatically transmit the updated image data to the storage device 140 to be stored in the data address. More descriptions regarding the updating of the image data stored in the data address may be found elsewhere in the present disclosure. See, e.g., 604 and relevant descriptions thereof.

Figure 5:
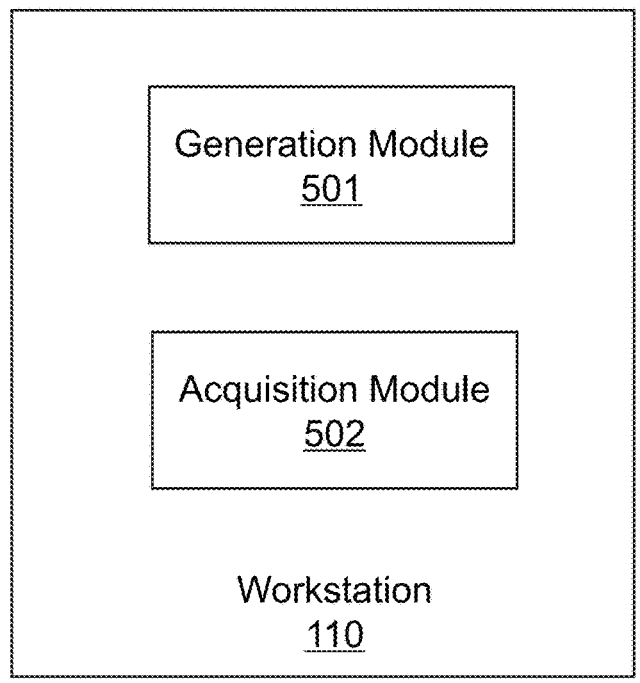
FIG. 5 is a block diagram illustrating an exemplary workstation according to some embodiments of the present disclosure.

FIG. 5 is a block diagram illustrating an exemplary workstation 110 according to some embodiments of the present disclosure. The workstation 110 may be communicated with the storage device 140 that is accessible to the workstation 110 and the user terminal 130. As shown in FIG. 4, the workstation 110 may include a generation module 501 and an acquisition module 502.

The generation module 501 may be configured to generate an identifier relating to a subject. In some embodiments, the subject may include an ROI. In some embodiments, the identifier may point to a data address in the storage device 140 that stores data relating to the subject. In some embodiments, the identifier may include a barcode, a QR code, a text identifier, an image identifier, or the like, or any combination thereof. In some embodiments, the generation module 501 may generate the identifier based on the data relating to the subject.

The generation module 501 may also be configured to generate a processing result by processing an updated image data acquired by the acquisition module 502. For example, the processing result may include a treatment plan directed to the ROI. Merely by way of example, the ROI may include a tumor region of the subject. The treatment plan may describe how the radiotherapy treatment is planned to be performed on the subject, more specifically, how one or more beams are delivered to the tumor region of the subject during each treatment fraction over the course of treatment lasting a certain period of time, e.g., days. More descriptions regarding the generation of the identifier and the processing result may be found elsewhere in the present disclosure. See, e.g., 601, 606, and relevant descriptions thereof.

The acquisition module 502 may be configured to acquire the updated image data stored in the data address. For example, the acquisition module 502 may access the data address and retrieve the updated image data from the data address. More descriptions regarding the acquisition of the updated image data may be found elsewhere in the present disclosure. See, e.g., 605 and relevant descriptions thereof.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the user terminal 130 and/or the workstation 110 may include one or more additional modules, such as a storage module (not shown) for storing data. As another example, one or more modules of the user terminal 130 and/or the workstation 110 described above may be omitted. Additionally or alternatively, two or more modules of the user terminal 130 and/or the workstation 110 may be integrated into a single component. A module of the user terminal 130 and/or the workstation 110 may be divided into two or more units.

Figure 6:
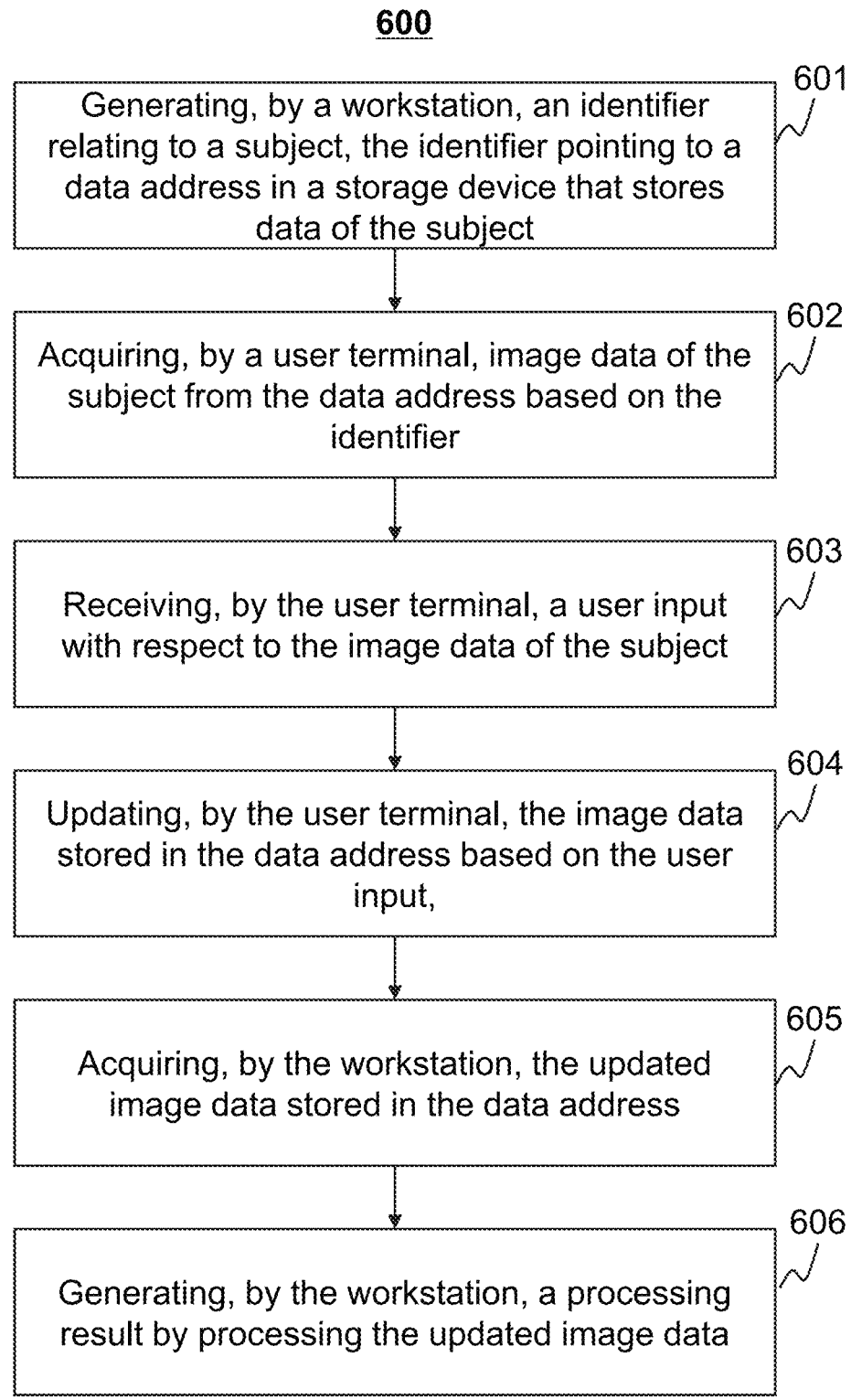
FIG. 6 is a flowchart illustrating an exemplary process for generating a processing result relating to a subject according to some embodiments of the present disclosure.

FIG. 6 is a flowchart illustrating an exemplary process for generating a processing result relating to a subject according to some embodiments of the present disclosure. In some embodiments, process 600 may be executed by the system 100, which may include the workstation 110, the user terminal 130, and the storage device 140 as described in connection with FIG. 1. For example, the process 600 may be implemented as a set of instructions (e.g., an application) stored in a storage device (e.g., the storage device 140, the storage device 220, and/or the storage 390). In some embodiments, the workstation 110 (e.g., a processing device of the workstation 110, the processor 210 of the computing device 200, and/or one or more modules illustrated in FIG. 5) and the user terminal 130 (e.g., a processing device of the user terminal 130, the processor 210 of the computing device 200, and/or one or more modules illustrated in FIG. 4) may execute the set of instructions and may accordingly be directed to perform the process 600. The storage device 140 may be accessible to both the workstation 110 and the user terminal 130, so as to realize a data synchronization between the workstation 110 and the user terminal 130.

In some embodiments, the workstation 110 and the user terminal 130 may be connected to and communicated with each other. For example, the connection between the workstation 110 and the user terminal 130 may be previously established. In some embodiments, the workstation 110 may be connected to a plurality of user terminals. The user terminal 130 may be selected from the user terminals, for example, randomly or by a user (e.g., a doctor). Merely by way of example, the workstation 110 may display the connected user terminals. The user may select a specific user terminal from the user terminals, for example, by inputting an ID number of the specific user terminal into the workstation 110. The specific user terminal selected by the user may be designated as the user terminal 130. Alternatively, the connection between the workstation 110 and the user terminal 130 may be established before the implementation of the process 600. For example, the user terminal 130 may send a connection request to the workstation 110, for example, by scanning a quick response (QR) code displayed by the workstation 110. The connection between the workstation 110 and the user terminal 130 may be established according to the connection request.

In 601, the workstation 110 (e.g., the generation module 501) may generate an identifier relating to the subject.

As used herein, the subject may include a biological subject (e.g., a patient, a cell, a tissue, an organ) and/or a non-biological subject. In some embodiments, the subject may include an ROI. The ROI may be any physical portion of the subject, such as, one or more organs or tissues. In some embodiments, the ROI may include a region of the subject including at least part of malignant tissue (e.g., a tumor, a cancer-ridden organ, or a non-cancerous target of radiation therapy) and/or other tissue (e.g., a tissue surrounding the malignant tissue). For example, the ROI may include a target and/or one or more organs-at-risk (OAR). A target may refer to a certain anatomical structure that needs to be tracked and/or monitored during a radiotherapy treatment. For example, the target may be a tumor, an organ with a tumor, a tissue with a tumor, or any combination thereof, that needs to be treated by radiations. An OAR may include an organ (or a portion thereof) and/or a tissue that are close to the target and not intended to be subjected to radiation but under the risk of radiation damage due to its proximity to the target.

In some embodiments, the subject to be analyzed may be selected by a user (e.g., a doctor) via the user terminal 130. For example, the user may input identity information (e.g., a name and/or an ID card number) of the subject into the user terminal 130 via, such as, a mouse, a touch screen, or a speech input component. The identity information of the subject may be transmitted to the workstation 110 for identifying the subject. Alternatively, the subject to be analyzed may be selected by the workstation 110 itself. Merely by way of example, the workstation 110 may determine a patient who is being scanned or to be treated as the subject.

In some embodiments, the identifier may point to a data address in the storage device 140 that stores data relating to the subject. The data address may indicate a location in the storage device that stores data relating to the subject. Through the data address, the data relating to the subject may be accessed. For example, the data address may include a file path directed to a specific file corresponding to the subject in a file system. As another example, the data address may include a uniform resource locator (URL). As described in connection with FIG. 1, the data relating to the subject may include basic data, medical record data, medical examination data, image data, or the like, or any combination thereof, of the subject.

In some embodiments, the identifier may include a barcode, a QR code, a text identifier, an image identifier, or the like, or any combination thereof. In some embodiments, the identifier may include the data or a portion of the data relating to the subject. For example, the text identifier may include the name, the gender, the nickname, the age, the phone number, the ID card number, the bed number, the room number, or the like, or any combination thereof, of the subject. As another example, the image identifier may include a head portrait, a fingerprint, a photo, a medical image, or the like, or any combination thereof, of the subject.

In some embodiments, the workstation 110 may generate the identifier based on the data relating to the subject. For example, the workstation 110 may generate the text identifier based on the basic data of the subject. As another example, the workstation 110 may generate the image identifier based on the basic data and/or the image data of the subject. In some embodiments, the workstation 110 may generate the identifier (e.g., the barcode and the QR code) using an encoding technique. Alternatively, the identifier may be generated previously and stored in a storage device (e.g., a storage of the workstation 110, the storage device 140, the storage device 220, and/or the storage 390). For example, the workstation 110 may generate the identifiers of a plurality of subjects and store the identifiers into the storage device. The workstation 110 may determine the identifier corresponding to the subject to be analyzed from of the identifiers of the plurality of subjects, for example, according to the data relating to the subject.

In some embodiments, after the identifier is generated or obtained, the workstation 110 may display the identifier on a display of the workstation 110.

In 602, the user terminal 130 (e.g., the acquisition module 401) may acquire image data of the subject from the data address based on the identifier.

For example, the image data may include one or more images of the subject (or a portion thereof) acquired by a biomedical imaging system as described elsewhere in this disclosure, such as an MRI system, a CT system. In some embodiments, the image data may include a target image of the subject. As used herein, a target image refers to an image that needs to be processed. The target image may include a 2D image (e.g., a slice image), a 3D image, a 4D image (e.g., a series of 3D images over time), and/or any related image data (e.g., scan data, projection data), or the like. For example, the target image may include a newly-generated image of the subject, an image of a specific portion (e.g., a lung) of the subject, an image acquired by a specific imaging modality (e.g., a CT imaging modality), or the like, or any combination thereof. In some embodiments, the user may input a condition that the target image needs to satisfy (e.g., a condition relating to an imaging modality, an imaging portion, an imaging time) into the user terminal 130. The target image may be acquired by the user terminal 130 according to the condition of the target image. In some embodiments, the image data may include one or more target images of the subject. For example, the user terminal 130 may obtain two target images that are generated at different imaging times.

In some embodiments, the user terminal 130 may access to the data address based on the identifier, and then obtain the image data (e.g., the target image) from the data address. For example, the user terminal 130 may obtain the image data of the subject by scanning the identifier. Merely by way of example, the user terminal 130 may include a camera, and the camera may be used to scan the identifier displayed by the workstation 110. By scanning the identifier, the user terminal 130 may access the data address corresponding to the identifier and acquire the image data of the subject from the data address. In some embodiments, whether the user terminal 130 can access the data address may relate to a signal condition of the user terminal 130 (e.g., the stability of the connection between the storage device 140 and the user terminal 130), an access permission of the user terminal 130 with respect to the storage device 140, etc.

In some embodiments, after the user terminal 130 scans the identifier, the storage device 140 may automatically transmit the image data of the subject to the user terminal 130. Alternatively, after the user terminal 130 scans the identifier, the workstation 110 may acquire the image data of the subject from the storage device 140 and transmit the image data of the subject to the user terminal 130. Alternatively, after the user terminal 130 scans the identifier, it may send an information acquisition request to the workstation 110 or the storage device 140. In response to the information acquisition request, the workstation 110 or the storage device 140 may retrieve the image data of the subject from the data address and transmit the image data to the user terminal 130.

In some embodiments, the data stored in the data address may include a plurality of candidate images of the subject.

The user terminal 130 may access the data address based on the identifier, for example, by scanning the identifier. The user terminal 130 may further select the target image from the plurality of candidate images stored in the data address. Merely by way of example, the user terminal 130 may select the target image according to information relating to the candidate images (e.g., an imaging modality that generates each candidate image), information relating to the user (e.g., a department that the user belongs to), information relating to the workstation 110 (e.g., computational tasks assigned to the workstation 110), or the like, or any combination thereof. For example, the user terminal 130 may select a CT image among the candidate images as the target image. As another example, the candidate images may be assigned to a plurality of users for processing, the user terminal 130 may select the candidate image that is assigned to the user who operates the user terminal 130 as the target image. As still another example, the candidate images may be assigned to a plurality of workstations for processing, and the user terminal 130 may select the candidate image assigned to the workstation 130 as the target image.

In some embodiments, the user terminal 130 may also acquire other data, such as the basic data, the medical record data, and/or the medical examination data of the subject from the data address.

In 603, the user terminal 130 (e.g., the acquisition module 401) may receive a user input with respect to the image data of the subject.

The user input may include, for example, an annotation added to the target image, a modification of the target image, a confirmation regarding the target image, a comment regarding the target image, or the like, or any combination thereof. For example, the user input may include an annotation regarding the ROI of the subject in the target image. The annotation regarding the ROI may include, such as, a bounding box enclosing the ROI, an annotation relating to the location of the ROI, an annotation relating to the shape of the ROI, an annotation relating to the size of the ROI, or the like, or any combination thereof. The bounding box may have the shape of a square, a rectangle, a triangle, a polygon, a circle, an ellipse, an irregular shape, or the like. The annotation may be in the form of a line, a curve, a graph, text, a parameter, or the like, or any combination thereof. Merely by way of example, the user may draw the contour of the ROI by a curve. As another example, the user may input one or more parameters relating to the contour of the ROI, such as the size and/or the shape of the ROI. In some embodiments, the annotation regarding the ROI may be used in, for example, image segmentation (e.g., an organ segmentation), a landmark localization, disease evaluation, and/or treatment planning. For example, the annotation regarding the ROI may be used to determine a radiation dose toward the ROI. In some embodiments, the annotation regarding the ROI may relate to the contour of the ROI.

The modification of the target image may include, for example, a modification regarding a signal to noise ratio (SNR) of the target image (for example, through an image denoising algorithm), a modification regarding one or more display parameters (e.g., the brightness, the contrast ratio) of the target image, or the like. The confirmation regarding the target image may include, for example, a determination as to whether the target image is suitable for processing, whether the target image has a desired image quality, or the like. The comment regarding the target image may include, for example, a comment regarding the image quality of the target image, a comment regarding the ROI (e.g., an abnormal state of the ROI), or the like.

In some embodiments, the user terminal 130 may include a touch screen. The user input may be inputted into the user terminal 130 via the touch screen. For example, the user may use a handwriting pen to annotate the contour of the ROI, which may be convenient and improve the contouring accuracy of the ROI. In some embodiments, the annotation regarding the ROI may be used in generating a treatment plan directed to the ROI. An accurate annotation of the contour of the ROI may improve the accuracy of the treatment plane, which, in turn, may improve the precision of treatment delivery and reduce or avoid unnecessary damages to the subject caused by inaccurate radiation delivery to the subject.

In some embodiments, the user terminal 130 may determine an input setting with respect to the user input based on feature information relating to the subject. Merely by way of example, the user input may include an annotation regarding the ROI. Exemplary feature information relating to the subject may include a size of the ROI, a shape of the ROI, a type of the ROI (e.g., whether the ROI is a target or an OAR), a location of the ROI, or the like, or any combination thereof. The input setting may include, for example, an annotation method (e.g., an automatic annotation method, a manual annotation method, a semi-automatic annotation method), the format of the annotation regarding the ROI, or the like, or any combination thereof.

In some embodiments, using an automatic annotation method, the user terminal 130 may receive an instruction from the user, and automatically annotate the target image of the subject according to an image analysis algorithm (e.g., a contour detection algorithm). For instance, a machine learning algorithm may be used to detect one or more ROIs and the contour(s) the ROI(s). Using a semi-automatic annotation method, the target image of the subject may be annotated by the user terminal 130 based on the image analysis algorithm in combination with user intervention (e.g., an edit of a contour detected by the user terminal 130 by the user). Using a manual annotation method, the target image of the subject may be annotated manually by the user. The format of the annotation may relate to, for example, a shape of the annotation (e.g., an arrow, a curve, a circle), a color of the annotation, a thickness of the annotation, etc. Merely by way of example, the user terminal 130 may use different colors to annotate different ROIs (e.g., a target and an OAR). Additionally or alternatively, the user terminal 130 may determine the shape and the thickness of the annotation according to the size of the ROI. In some embodiments, the input setting may be determined according to a default setting of the user terminal 130 and/or preference information of the user of the user terminal 130.

In 604, the user terminal 130 (e.g., the updating module 402) may update the image data stored in the data address based on the user input.

In some embodiments, the user terminal 130 may generate the updated image data based on the image data of the subject and the user input. For example, the user terminal 130 may add the annotation regarding the ROI to the target image, and the updated image data may include the target image with the annotation. As another example, the user terminal 130 may update the image data by modifying one or more display parameters of the target image. As another example, the user terminal 130 may add the confirmation and/or the comment regarding the target image to the target image. Then, the user terminal 130 may cause the storage device 140 to store the updated image data to the data address.

In some embodiments, the user terminal 130 may access the data address based on the identifier, and store the updated image data into the data address. For example, the user terminal 130 may access the data address by scanning the identifier. The user terminal 130 may replace the original image data in the data address with the updated image data. Alternatively, the user terminal 130 may store the updated image data in the data address without removing the original image data. In some embodiments, the identifier may be displayed on the workstation 110 during the operations 602-604. Alternatively, after the user terminal 130 scans the identifier in 602, the workstation 110 may stop displaying the identifier; and after the user terminal 130 updates the image data stored in the data address, the workstation 110 may redisplay the identifier. In some embodiments, the workstation 110 may generate a second identifier different from the identifier, wherein the second identifier may also point to the data address. The user terminal 130 may access the data address by scanning the second identifier, and store the updated image data into the data address.

In some embodiments, after the updated image data is generated by the user terminal 130, the user terminal 130 may automatically transmit the updated image data to the storage device 140 to be stored in the data address. In other words, the data stored in the data address corresponding to the subject may be automatically synchronized after the user terminal 130 updates the image data of the subject.

In 605, the workstation 110 (e.g., the acquisition module 502) may acquire the updated image data stored in the data address.

For example, the workstation 110 may access the data address and retrieve the updated image data from the data address. As another example, the workstation 110 may send an information acquisition request regarding the data address to the storage device 140, and the storage device 140 may transmit the updated image data to the workstation 110 in response to the information acquisition request. As yet another example, after the updated image data is stored in the data address, it may be transmitted to the workstation 110 automatically.

In 606, the workstation 110 (e.g., the generation module 501) may generate the processing result by processing the updated image data.

For example, the processing result may include a treatment plan directed to the ROI. Merely by way of example, the ROI may include a tumor region of the subject. The treatment plan may describe how the radiotherapy treatment is planned to be performed on the subject, more specifically, how one or more beams are delivered to the tumor region of the subject during each treatment fraction over the course of treatment lasting a certain period of time, e.g., days. For example, the treatment plan may provide a total dose (e.g., 0.1 Gy, 10 Gy, 50 Gy, 100 Gy, etc.) and a dose distribution in the target. In some embodiments, the workstation 110 may generate the treatment plan by using an RT software, e.g., a Pinnacle RT plan software, an Eclipse RT plan software, an Oncentral RT plan software.

As another example, the workstation 110 may perform one or more image processing operations on the updated image data. Exemplary image processing operations may include the image segmentation, the landmark localization, or the like.

Conventionally, a medical imaging system usually may include a workstation for data processing and a user terminal for enabling user interaction. For example, an RT system, which includes a user terminal and a workstation, is widely used in clinical treatment for cancers and other conditions. In some occasions, data synchronization needs to be performed between the user terminal and the workstation. For example, if a storage device is connected to an LAN, the user terminal and the workstation have to connect to the LAN and get an access permission to the storage device, so as to acquire data from the storage device. If the user terminal modifies the acquired data, it may need to upload the modified data to the storage device, and the workstation may need to connect to the LAN and get the access permission to the storage device to acquire the modified data, which has a low efficiency.

According to some embodiments of the present disclosure, the user terminal 130 may access the data address corresponding to the subject by scanning the identifier pointing to the data address to obtain the image data from the data address. After the updated image data is generated by the user terminal 130, the user terminal 130 may automatically transmit the updated image data to the storage device 140 to be stored in the data address. After the updated image data is stored in the data address, it may be transmitted to the workstation 110 automatically. In some embodiments, the storage device 140 may be part of the workstation 110. For example, the storage device 140 may be a cache region of the workstation 110 shared with the user terminal. The user terminal 130 may have a permission to access data stored in the cache region and/or upload data into the cache region. In such cases, once the user terminal 130 generates new data based on a user input (e.g., an updated image of a subject with an annotation regarding an ROI of the subject), it can upload the new data into the cache region, and the new data may be automatically synchronized with the workstation 110. Thus, through the storage device 140, data synchronization between the workstation 110 and the user terminal 130 may be realized, which may effectively prevent loss of data (e.g., because the new data generated by the user terminal 130 may be transmitted to the storage device 140 automatically) and improve the efficiency of the data transmission and the data synchronization.

It should be noted that the above description regarding the process 600 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the process 600 may be accomplished with one or more additional operations not described and/or without one or more of the operations discussed above. For example, after 606, the workstation 110 may store the processing result in the storage device 140. As another example, the user terminal 130 may obtain the processing result from the workstation 110 and/or the storage device 140, and display the processing result.

Figure 7:
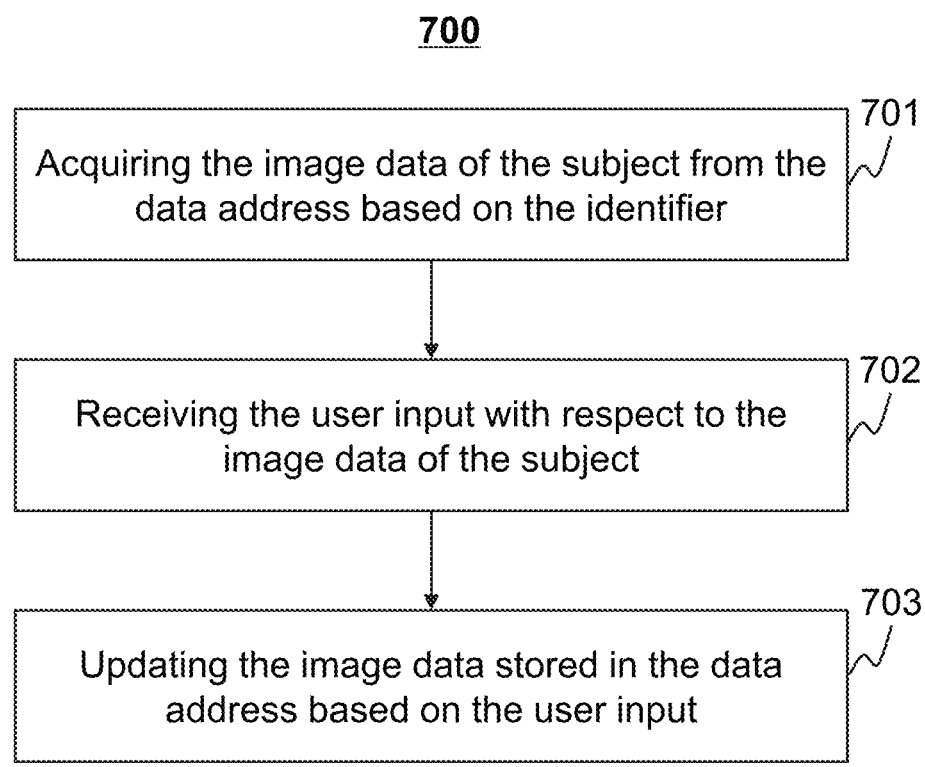
FIG. 7 is a flowchart illustrating an exemplary process for updating image data stored in a data address in a storage device according to some embodiments of the present disclosure.

FIG. 7 is a flowchart illustrating an exemplary process for updating image data stored in a data address in a storage device according to some embodiments of the present disclosure. In some embodiments, process 700 may be executed by the user terminal 130 of the data synchronization system 100. For example, the process 700 may be implemented as a set of instructions (e.g., an application) stored in a storage device (e.g., the storage device 140, the storage device 220, and/or the storage 390). In some embodiments, the user terminal 130 (e.g., a processing device of the user terminal 130, the processor 210 of the computing device 200, and/or one or more modules illustrated in FIG. 4) may execute the set of instructions and may accordingly be directed to perform the process 700. The user terminal 130 may be communicated with the storage device 140 that is accessible to the user terminal 130 and the workstation 110.

In 701, the user terminal 130 (e.g., the acquisition module 401) may acquire image data of a subject from a data address in the storage device 140 that stores data of the subject based on an identifier.

For example, the identifier may be generated by the workstation 110 and point to the data address. The user terminal 130 may acquire the image data by performing operation 602 as described in connection with FIG. 6.

In 702, the user terminal (e.g., the acquisition module 401) may receive a user input with respect to the image data of the subject.

Operation 702 may be performed in a similar manner as operation 603, and the descriptions thereof are not repeated here.

In 703, the user terminal (e.g., the updating module 402) may update the image data stored in the data address based on the user input.

Operation 703 may be performed in a similar manner as operation 604 and the descriptions thereof are not repeated here.

Figure 8:
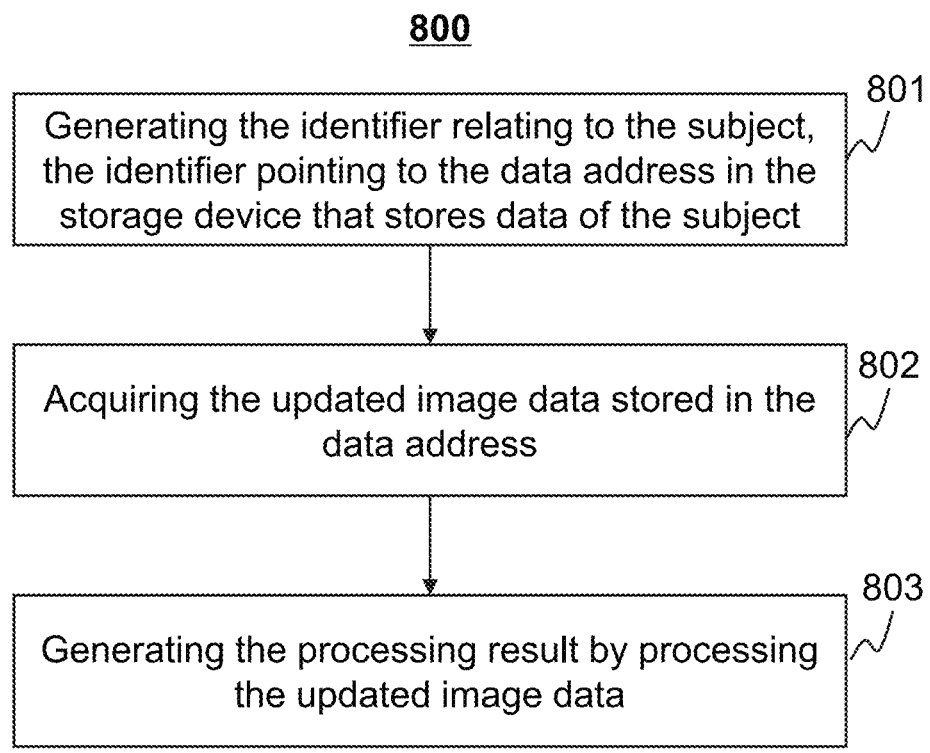
FIG. 8 is a flowchart illustrating an exemplary process for generating a processing result relating to a subject according to some embodiments of the present disclosure.

FIG. 8 is a flowchart illustrating an exemplary process for generating a processing result relating to a subject according to some embodiments of the present disclosure. In some embodiments, process 800 may be executed by the workstation 110 of the data synchronization system 100. For example, the process 800 may be implemented as a set of instructions (e.g., an application) stored in a storage device (e.g., the storage device 140, the storage device 220, and/or the storage 390). In some embodiments, the workstation 110 (e.g., a processing device of the workstation 110, the processor 210 of the computing device 200, and/or one or more modules illustrated in FIG. 5) may execute the set of instructions and may accordingly be directed to perform the process 800. The workstation 110 may be communicated with the storage device 140 that is accessible to the workstation 110 and the user terminal 130.

In 801, the workstation 110 (e.g., the generation module 501) may generate an identifier relating to a subject.

Operation 801 may be performed in a similar manner as operation 601, and the descriptions thereof are not repeated here.

The image data of the subject may be acquired by the user terminal 130 from the data address based on the identifier. A user input with respect to the image data of the subject may be inputted into the user terminal 130. The image data stored in the data address may be updated by the user terminal 130 based on the user input.

In 802, the workstation 110 (e.g., the acquisition module 502) may acquire the updated image data stored in the data address.

Operation 802 may be performed in a similar manner as operation 605, and the descriptions thereof are not repeated here.

In 803, the workstation 110 (e.g., the generation module 501) may generate a processing result by processing the updated image data.

Operation 803 may be performed in a similar manner as operation 606, and the descriptions thereof are not repeated here.

It should be noted that the above description regarding the process 700 and the process 800 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the process 700 and/or the process 800 may be accomplished with one or more additional operations not described and/or without one or more of the operations discussed above.

Figure 9:
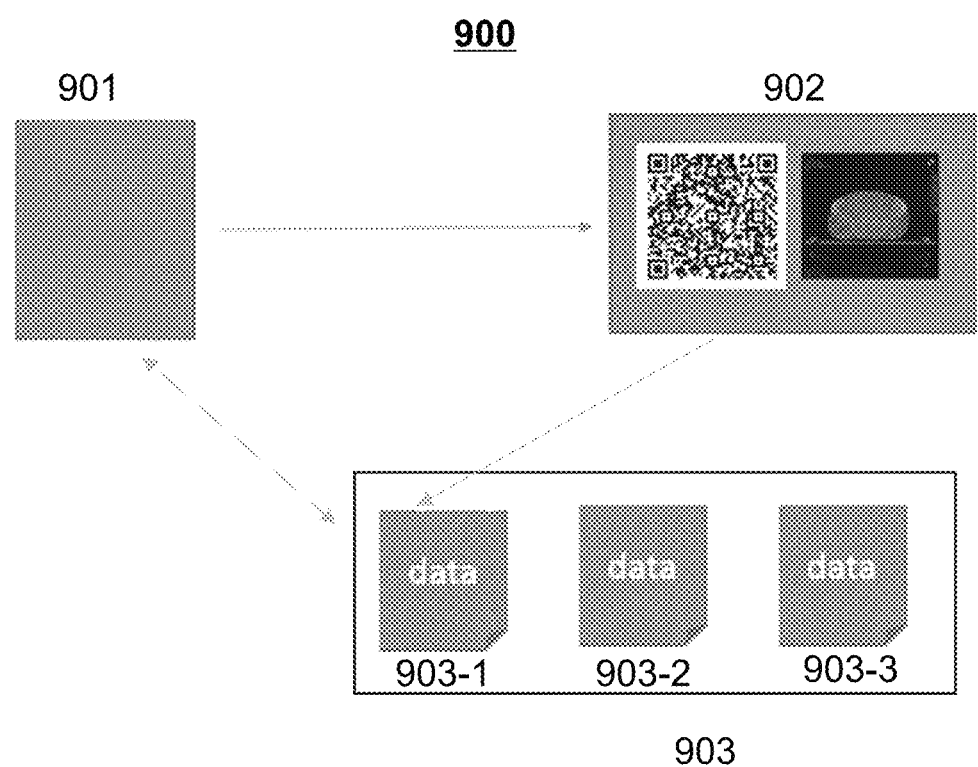
FIG. 9 is a diagram illustrating an exemplary data synchronization system according to some embodiments of the present disclosure.

FIG. 9 is a diagram illustrating an exemplary data synchronization system 900 according to some embodiments of the present disclosure. The data synchronization system 900 may be an exemplary data synchronization system 100 as described in connection with FIG. 1. As shown in FIG. 9, the data synchronization system 900 may include a tablet 901, a workstation 902, and a storage device 903. The storage device 903 may include a data address 903-1, a data address 903-2, a data address 903-3, etc. The user terminal 901 and the workstation 902 may be connected to the storage device 903 via, for example, a Bluetooth™ network, a Wi-Fi network.

In some embodiments, a user may open an RT plan software installed in the workstation 902 and select a subject to be analyzed via the RT plan software. The workstation 902 may then display a QR code and/or an image identifier of the subject. The identifier may point to the data address 903-1 in the storage device 903 that stores data relating to the subject. The user may use a camera of the user terminal 901 to scan the QR code or the image identifier, so as to acquire image data of the subject from the data address 903-1. The user terminal 901 may receive a user input with respect to the image data of the subject and update the image data stored in the data address 903-1 based on the user input. The workstation 902 may acquire the updated image data stored in the data address 903-1 and generate a processing result based on the updated image data. In some embodiments, the storage device 903 may be part of the workstation 902, for example, be a cache region of the workstation 902.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB.NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed object matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±1%, ±5%, ±10%, or ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting effect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A system for data synchronization, comprising:
   a workstation;
   a user terminal; and
   a storage device that is a cache region of the workstation shared with the user terminal, being accessible to the user terminal and the workstation, wherein
   the workstation is configured to generate an identifier relating to a subject, the identifier pointing to a data address in the storage device that stores data relating to the subject, the identifier includes at least one of a barcode, a quick response (QR) code, or an image identifier; and the workstation is configured to display the identifier on a display of the workstation;
   the user terminal is configured to acquire image data of the subject from the data address by scanning the identifier, receive a user input with respect to the image data of the subject, generate updated image data based on the user input, and transmit the updated image data to the storage device to be stored in the data address by scanning the identifier again; and the updated image data is automatically synchronized with the workstation after the updated image data is stored in the data address, and the workstation is further configured to generate a processing result by processing the updated image data, the processing result includes a treatment plan that includes at least one of a total dose or a dose distribution in the subject, the workstation is configured to generate the treatment plan by using an RT software.

2. The system of claim 1, wherein the user input includes an annotation regarding a region of interest (ROI) of the subject in the image data.

3. The system of claim 2, wherein the treatment plan is directed to the ROI.

4. The system of claim 1, wherein the data stored in the data address includes a plurality of candidate images of the subject, and
to acquire the image data of the subject based on the identifier, the user terminal is configured to:
access the data address by scanning the identifier; and
select a target image from the plurality of candidate images stored in the data address.

5. The system of claim 1, wherein the user terminal is further configured to:
determine, based on feature information relating to the subject, an input setting with respect to the user input.

6. The system of claim 1, wherein the user input is inputted into the user terminal via a handwriting pen.

7. A method for data synchronization implemented on a user terminal, the user terminal being communicated with a storage device that is a cache region of a workstation, the storage device being accessible to the user terminal and the workstation, the method comprising:
acquiring, by scanning an identifier relating to a subject, image data of the subject from a data address in the storage device that stores data relating to the subject, wherein the identifier is generated and displayed by the workstation and points to the data address, the identifier includes at least one of a barcode, a quick response (QR) code, or an image identifier;
receiving a user input with respect to the image data of the subject;
generating updated image data based on the user input; and
transmitting the updated image data to the storage device to be stored in the data address by scanning the identifier again, wherein the storage device is a cache region of the workstation shared with the user terminal, the updated image data is automatically synchronized with the workstation after the updated image data is stored in the data address, and the workstation is further configured to generate a processing result by processing the updated image data, the processing result includes a treatment plan that includes at least one of a total dose or a dose distribution in the subject, the workstation is configured to generate the treatment plan by using an RT software.

8. The method of claim 7, wherein the user input includes an annotation regarding a region of interest (ROI) of the subject in the image data.

9. The method of claim 8, wherein the treatment plan is directed to the ROI.

10. The method of claim 7, wherein the data stored in the data address includes a plurality of candidate images of the subject, and
the acquiring, based on an identifier relating to the subject, image data of a subject from a data address in the storage device that stores data of the subject comprises:
accessing the data address by scanning the identifier; and
selecting a target image from the plurality of candidate images stored in the data address.

11. The method of claim 7, further comprising:
determining, based on feature information relating to the subject, an input setting with respect to the user input.

12. The method of claim 7, wherein the user input is inputted into the user terminal via a handwriting pen.

13. A method for data synchronization implemented on a workstation, a storage device that is a cache region of the workstation being shared with a user terminal, the storage device being accessible to the user terminal and the workstation, the method comprising:
generating an identifier relating to a subject, the identifier pointing to a data address in the storage device that stores data relating to the subject, the identifier includes at least one of a barcode, a quick response (QR) code, or an image identifier;
displaying the identifier on a display of the workstation, wherein image data of the subject is acquired by the user terminal from the data address by scanning the identifier, a user input with respect to the image data of the subject is received by the user terminal, updated image data is generated based on the user input by the user terminal, and the updated image data is transmitted to the storage device to be stored in the data address by the user terminal scanning the identifier again, the storage device is a cache region of the workstation shared with the user terminal, the updated image data is automatically synchronized with the workstation after the updated image data is stored in the data address; and
acquiring the updated image data stored in the data address and generating a processing result by processing the updated image data, the processing result includes a treatment plan that includes at least one of a total dose or a dose distribution in the subject, the treatment plan is generated by using an RT software.

14. The method of claim 13, wherein the user input includes an annotation regarding a region of interest (ROI) of the subject in the image data.

15. The method of claim 14, wherein the treatment plan is directed to the ROI.

16. The method of claim 13, wherein the data stored in the data address includes a plurality of candidate images of the subject, and
to acquire the image data of the subject based on the identifier, the user terminal is configured to:
access the data address by scanning the identifier; and
select a target image from the plurality of candidate images stored in the data address.

* * * * *